(12) United States Patent
Bernhardt et al.

(10) Patent No.: US 11,974,873 B2
(45) Date of Patent: May 7, 2024

(54) METHOD FOR THE AUTOMATIC REGULATION OF RADIATION DOSES OF MEDICAL X-RAY DEVICES

(71) Applicant: Siemens Healthcare GmbH, Erlangen (DE)

(72) Inventors: Philipp Bernhardt, Forchheim (DE); Gregor Niewalda, Buckenhof (DE); Michael Wiets, Langensendelbach (DE)

(73) Assignee: Siemens Healthineers AG, Forchheim (DE)

( * ) Notice: Subject to any disclaimer, the term of this patent is extended or adjusted under 35 U.S.C. 154(b) by 133 days.

(21) Appl. No.: 17/089,890

(22) Filed: Nov. 5, 2020

(65) Prior Publication Data
US 2021/0137482 A1     May 13, 2021

(30) Foreign Application Priority Data
Nov. 12, 2019 (DE) ..................... 10 2019 217 421.3

(51) Int. Cl.
*A61B 6/00* (2006.01)
*A61B 6/58* (2024.01)
(Continued)

(52) U.S. Cl.
CPC .............. *A61B 6/545* (2013.01); *A61B 6/542* (2013.01); *A61B 6/582* (2013.01); *G16H 40/67* (2018.01); *G16H 70/20* (2018.01)

(58) Field of Classification Search
CPC ....... A61B 6/4441; A61B 6/542; A61B 6/545; A61B 6/582; G16H 70/20; G16H 50/30;
(Continued)

(56) References Cited

U.S. PATENT DOCUMENTS 6,233,310 B1 * 5/2001 Relihan ..................... H05G 1/46
378/108
9,420,985 B2 * 8/2016 Watanabe ............. A61B 6/5217
(Continued)

FOREIGN PATENT DOCUMENTS

CN     1593342 A     3/2005
CN    103462628 A    12/2013
(Continued)

OTHER PUBLICATIONS

Verfahren zur Optimierung der automatischen Belichtungsregelung bezüglich Effektiv- und Benutzerdosen in der röntgenbasierten, medizinischen Bildgebung; German Office Action for German Application No. 102019217421.3 dated Jul. 13, 2020.

*Primary Examiner* — Dani Fox
*Assistant Examiner* — Soorena Kefayati
(74) *Attorney, Agent, or Firm* — Harness, Dickey & Pierce, P.L.C.

(57) ABSTRACT

A method is for the automatic regulation of radiation doses of a person for an examination with a medical X-ray device, which has a first dose regulation. In an embodiment, the method includes a specification of X-ray parameters of an X-ray examination based upon patient information and a specification of a dose regulation as a function of X-ray parameters as well as a limit value for deterministic radiation damage and/or a guide value for stochastic effective doses.

23 Claims, 3 Drawing Sheets

(51) Int. Cl.
*G16H 40/67* (2018.01)
*G16H 70/20* (2018.01)

(58) Field of Classification Search
CPC .......... A61N 5/1031; A61N 2005/1032; A61N 2005/1034; A61N 2005/1035
See application file for complete search history.

(56) References Cited

U.S. PATENT DOCUMENTS

| | | | | |
|---|---|---|---|---|
| 9,649,079 | B1* | 5/2017 | Guntzer | G06T 7/0012 |
| 9,931,091 | B2* | 4/2018 | Watanabe | A61B 6/4441 |
| 2005/0058250 | A1 | 3/2005 | Popescu et al. | |
| 2005/0116172 | A1* | 6/2005 | Trinkaus | G16H 70/20 |
| | | | | 250/363.02 |
| 2008/0103834 | A1* | 5/2008 | Reiner | G16H 20/40 |
| | | | | 705/3 |
| 2008/0232542 | A1* | 9/2008 | Lin | A61B 6/032 |
| | | | | 378/16 |
| 2008/0317205 | A1* | 12/2008 | Inuga | A61B 6/4441 |
| | | | | 378/97 |
| 2009/0003527 | A1* | 1/2009 | Hoornaert | A61N 5/1048 |
| | | | | 378/97 |
| 2009/0279672 | A1* | 11/2009 | Reiner | A61B 6/581 |
| | | | | 378/207 |
| 2010/0239069 | A1* | 9/2010 | Bourdeaux | A61B 6/542 |
| | | | | 378/96 |
| 2011/0238434 | A1* | 9/2011 | Froehlich | G16H 80/00 |
| | | | | 705/2 |
| 2011/0270623 | A1* | 11/2011 | Reiner | G16H 30/40 |
| | | | | 705/2 |
| 2011/0317815 | A1* | 12/2011 | Bernhardt | A61B 6/542 |
| | | | | 378/98.5 |
| 2012/0022845 | A1* | 1/2012 | Bismuth | A61B 6/542 |
| | | | | 703/11 |
| 2012/0041685 | A1* | 2/2012 | Ding | A61N 5/1031 |
| | | | | 702/19 |
| 2012/0106817 | A1* | 5/2012 | Shih | A61B 6/583 |
| | | | | 382/131 |
| 2012/0148131 | A1 | 6/2012 | Couch et al. | |
| 2012/0213326 | A1* | 8/2012 | Walker | G16H 40/63 |
| | | | | 378/165 |
| 2014/0031603 | A1* | 1/2014 | Robar | A61B 6/06 |
| | | | | 600/1 |
| 2014/0079310 | A1* | 3/2014 | Nakatsugawa | A61B 6/542 |
| | | | | 382/132 |
| 2014/0270053 | A1* | 9/2014 | Larson | A61B 6/5258 |
| | | | | 378/4 |
| 2014/0304206 | A1* | 10/2014 | Lee | A61B 6/032 |
| | | | | 706/47 |
| 2014/0353514 | A1* | 12/2014 | Unfors | G01T 1/026 |
| | | | | 250/370.07 |
| 2015/0100290 | A1* | 4/2015 | Falt | G16H 50/50 |
| | | | | 703/2 |
| 2015/0238160 | A1 | 8/2015 | Flohr et al. | |
| 2015/0271903 | A1* | 9/2015 | Allmendiger | H05G 1/70 |
| | | | | 378/110 |
| 2015/0272532 | A1* | 10/2015 | Allmendinger | A61B 6/032 |
| | | | | 378/19 |
| 2015/0306423 | A1* | 10/2015 | Bharat | A61B 8/4218 |
| | | | | 600/1 |
| 2015/0356258 | A1* | 12/2015 | Moore | G16H 70/20 |
| | | | | 705/2 |
| 2015/0359503 | A1* | 12/2015 | Bernhardt | A61B 6/5258 |
| | | | | 378/19 |
| 2016/0038767 | A1* | 2/2016 | Wiersma | A61N 5/1031 |
| | | | | 378/204 |
| 2016/0073998 | A1* | 3/2016 | Shima | A61B 6/4476 |
| | | | | 378/64 |
| 2016/0114187 | A1* | 4/2016 | Ishii | A61N 5/1038 |
| | | | | 378/42 |
| 2016/0196406 | A1* | 7/2016 | Fält | A61B 6/10 |
| | | | | 703/2 |
| 2017/0007194 | A1* | 1/2017 | Bialkowski | A61B 6/469 |
| 2017/0095223 | A1* | 4/2017 | Tian | A61B 6/032 |
| 2017/0245825 | A1* | 8/2017 | Star-Lack | A61B 6/5217 |
| 2018/0144823 | A1* | 5/2018 | Raman | H04L 67/55 |
| 2018/0168534 | A1* | 6/2018 | Desponds | A61B 6/0407 |
| 2018/0271472 | A1* | 9/2018 | Ercan | A61B 6/467 |
| 2018/0289351 | A1* | 10/2018 | Dorn | A61B 6/542 |
| 2019/0298293 | A1* | 10/2019 | de Haan | A61B 6/542 |

FOREIGN PATENT DOCUMENTS

| | | |
|---|---|---|
| CN | 104856717 A | 8/2015 |
| CN | 107095689 A | 8/2017 |
| DE | 102010025512 A1 | 12/2011 |
| DE | 102014211150 A1 | 12/2015 |
| EP | 1977269 B1 | 11/2013 |

* cited by examiner

METHOD FOR THE AUTOMATIC REGULATION OF RADIATION DOSES OF MEDICAL X-RAY DEVICES

PRIORITY STATEMENT

The present application hereby claims priority under 35 U.S.C. § 119 to German patent application numbers DE 102019217421.3 filed Nov. 12, 2019, the entire contents of which are hereby incorporated herein by reference.

FIELD

Example embodiments generally relate to a method for the automatic regulation of radiation doses of a person through the use of a dose regulation, which is specified as a function of patient information and a limit value for deterministic radiation damage and/or a guide value for stochastic effective doses for an X-ray examination.

BACKGROUND

X-ray radiation has already been used in medical imaging for many decades. Through the irradiation (fluoroscopy) of an examination object using X-ray radiation and the measurement of the tissue penetration, it is possible to obtain structural information which e.g. can be used for the clinical diagnosis.

X-ray devices usually comprise one or more X-ray emitters with what are known as X-ray tubes, which generate the X-ray radiation. For this purpose, the X-ray tubes are operated by an X-ray generator with a voltage supply which makes available a high voltage required for operation. Depending on the absorption behavior of the examination object to be subjected to fluoroscopy, X-ray radiation is generated with different wavelengths in order to obtain sufficient delineation between different tissue types. In this context, the wavelength of the X-ray radiation may be adjusted via the voltage supplied to the X-ray tubes, for example. In order to achieve an optimal image quality, which is defined by the brightness, the contrast, the signal-to-noise ratio and the sharpness of the image for example, in particular the intensity of the X-ray radiation incident upon the region in question is of crucial importance.

In this context, the desired image quality of an X-ray examination must always be weighed against the radiation exposure of the patient. In principle: with a higher radiation dose, i.e. a larger number of X-ray quanta, it is possible to achieve an improved image quality, as what is known as the quantum noise decreases. Like any kind of ionizing radiation, however, X-ray radiation may lead to immediate damage in the tissue cells of the irradiated body regions of the patient, and is therefore also regulated by law on a country-specific basis. In particular, there are maximum permissible limit values for the radiation dose impinging on the body surface of a patient. This dose restriction, referred to as the entrance skin dose, is measured based upon a deterministic risk of damage to the skin surface of the patient. Below the limit value for deterministic damage, there is typically no risk for immediate damage, while radiation doses above the limit value may lead to immediate damage with a high probability.

Regardless of immediate radiation damage, each X-ray quantum possesses a potential risk of altering the genome of a cell. From these alterations, it is possible for tumors and cancer to develop over longer periods of time of up to 20 years. The risk of such a disease is also referred to as a stochastic risk. What are known as effective doses measure the stochastic risk of damage due to X-ray radiation in the overall body. In the case of stochastic damage, it is not possible to specify a specific limit value, as each individual radiation energy disposition has a low probability of leading to cancer. The more such events have taken place, the more probable is the occurrence of a disease. The risk of a disease due to stochastic radiation damage particularly increases disproportionately to the dose at high radiation doses.

In order to set the radiation dose of an X-ray examination in an appropriate manner and to avoid high radiation doses for patients, use can be made of various technical options. On the one hand, various parameters of the X-ray emitter, such as the tube voltage, the tube current, the X-ray prefiltering and the pulse width and the beam focus of the X-ray radiation can be adjusted for example. These parameters are used to influence not only the radiation dose but inter alia also the image contrast and the time resolution of the X-ray imaging. On the other hand, the distance between the patient and the radiation source can also be varied, in order to adjust the radiation dose for the patient. The dose irradiated onto a control area by an X-ray source decreases quadratically with the distance of the control area from the X-ray source. From this inverse square law and the limit value of the entrance skin dose, it is possible to specify a minimum distance from the focus point of the X-ray radiation source which the irradiated tissue has to at least assume in order to avoid deterministic damage.

The adjustment of the X-ray parameters to specific medical demands, such as a short pulse width in the case of a cardiological application for example, is generally subject to a fixed scheme and is taken into consideration by corresponding limit values of the X-ray parameters. A reduction of the radiation dose of the patient therefore must always take place with the consideration of application-specific X-ray parameters and thus places high demands on the regulation of the X-ray radiation source.

SUMMARY

At least one embodiment of the present invention reduces a radiation dose of a person during a medical examination with X-ray radiation. Advantageous embodiments are described in the claims.

The method according to at least one embodiment of the invention for specifying radiation doses of a person for an examination with a medical X-ray device, including a first dose regulation, comprises:
  specifying X-ray parameters of an X-ray examination based upon patient information; and
  specifying a dose regulation of the X-ray examination as a function of the X-ray parameters specified and at least one of a limit value for deterministic radiation damage and a guide value for stochastic effective doses.

The medical X-ray device according to an embodiment of the invention comprises a controller, the controller being configured to:
  specify X-ray parameters of an X-ray examination based upon patient information; and
  specify a dose regulation of the X-ray examination as a function of the X-ray parameters specified and at least one of a limit value for deterministic radiation damage and a guide value for stochastic effective doses.

The medical X-ray device according to an embodiment of the invention comprises:
  at least one processor configured to specify X-ray parameters of an X-ray examination based upon patient information; and specify a dose regulation of the X-ray examination as a function of the X-ray parameters specified and at least one of a limit value for deterministic radiation damage and a guide value for stochastic effective doses.

The non-transitory computer program product of at least one embodiment may be configured to carry out the method steps according to at least one embodiment of the invention via the computing unit. In this context, the computing unit must in each case have the requirements such as, for example, a corresponding RAM, a corresponding graphics card or a corresponding logic unit, in order to be able to carry out the respective method steps efficiently.

The non-transitory computer program product of at least one embodiment may be, for example, a non-transitory computer-readable medium.

BRIEF DESCRIPTION OF THE DRAWINGS

Further advantages and details of the present invention are presented in the an embodiment of embodiments described below and by reference to the drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory.

These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention for the automatic regulation of radiation doses of a person for an examination with a medical X-ray device comprises:

Specifying X-ray parameters of an X-ray examination based upon patient information. In this context, the X-ray examination can take place by way of any given medical X-ray device, such as a C-arm, a computed tomography scanner or a mammography device, for example. For example, patient information may represent an age, a body weight, a gender, a disease, a medical history and/or a body region in question, as well as a fluoroscopy angle of a patient. Based upon this patient information, it is possible to derive X-ray parameters for the X-ray method, which are to be set conservatively for a sufficient image quality. From the X-ray parameters, it is typically also possible to derive an irradiation interval as well as an irradiation power, from which a radiation dose of the X-ray examination can be determined. It is conceivable for the patient information to be allocated to multiple persons, whose patient information is available in a database.

In a further step, the specification of a dose regulation of the X-ray examination takes place as a function of X-ray parameters, as well as a limit value for deterministic radiation damage and/or a guide value for stochastic effective doses. A specification of a dose regulation means in particular that a regulation strategy for a radiation power of a patient is activated during an X-ray examination. The specified regulation strategy is preferably decisive for this X-ray examination. In this context, the limit values for deterministic radiation damage may be based on country-specific statutory provisions for the entrance skin dose in the patient. The guide value for stochastic effective doses is derived, in the context of the method according to the invention, from patient information, such as an age, a weight, a medical history or a treatment strategy which has been followed, for example. For this purpose, algorithms are preferably used which automatically extract the corresponding criteria from the patient information. It is likewise conceivable for corresponding criteria for specifying the guide value for stochastic effective doses to be entered manually by a physician or a member of medical personnel via a user interface of the medical X-ray device. Here, the guide value for stochastic effective doses is preferably less than or equal to the limit value for deterministic radiation damage.

As a function of the X-ray parameters, the limit value for deterministic radiation damage and/or the guide value for stochastic effective doses, it is possible to specify a dose regulation of an X-ray examination. A first dose regulation preferably has a parameter range which contains permissible X-ray parameter combinations of an X-ray examination. Possible X-ray parameters represent e.g. the voltage and the current of the X-ray tube, the quality of the beam focus as well as the use of filters and the distance of the patient from the X-ray radiation source. Moreover, any given combinations of the parameters mentioned and further options for adjusting the radiation dose of the patient are conceivable.

The method according to at least one embodiment of the invention in particular may also comprise a second dose regulation. In this context, the first dose regulation and the second dose regulation preferably have parameter ranges which are different from one another. Here, the sets of permitted parameters of the first dose regulation can be subsets of the permitted parameters of the second dose regulation. It is likewise conceivable for the permitted parameters of the first dose regulation to have intersections with the permitted parameters of the second dose regulation. Moreover, individual, multiple or all sets of permitted parameters of the first dose regulation may lie outside the sets of permitted parameters of the second dose regulation. It is likewise conceivable for the method to comprise a third or a fourth dose regulation, the parameter ranges of which are different or partially or completely overlap. In particular, the adjustment of the distance between patient and radiation source as well as the installation or setting of metal filters in the beam path may also take place manually by way of the medical personnel. The corresponding handling instructions for setting the X-ray parameters may be specified via a controller of the medical X-ray device and represented on a corresponding display unit for the medical personnel.

A radiation power of the X-ray examination may be constant or vary over time over the course of the X-ray examination. In this context, both a continuous and a discontinuous irradiation of the patient are conceivable. The dose regulation in particular specifies the radiation power in a discrete time step. Here, a radiation dose of an X-ray examination can be interpreted as the integral of the time-dependent radiation power, which is directed toward a body region of the patient with a defined mass. The specified radiation dose is preferably not exceeded during the course of the X-ray examination.

The method described in at least one embodiment advantageously makes it possible to adjust the X-ray parameters to individual patient requirements. By applying a dose regulation, the method in particular is robust and delivers reproducible results.

Further advantageous embodiments and developments of the invention emerge from the claims and the following description, wherein the independent claims of one claim category can also be developed similarly to the dependent claims of another claim category and the features of different example embodiments or variants can be combined to form new example embodiments.

According to one embodiment of the method according to the invention, a preliminary target dose is specified at least based upon patient information and/or X-ray parameters and/or an examination duration of an X-ray examination, wherein the specification of a dose regulation takes place as a function of a comparison of the preliminary target dose with a limit value for deterministic radiation damage and/or a guide value for stochastic effective doses. The preliminary target dose in particular represents a quantification of a radiation exposure, which can be monitored over any given periods of time. The preliminary target dose can therefore be compared in a simple manner with the limit value for deterministic radiation damage, which likewise describes a radiation dose.

An examination duration of an X-ray examination may e.g. represent a measured period of time or a period of time usually to be set for the performance of an X-ray examination. It is likewise conceivable for the preliminary target dose to be specified as a function of patient information, by a radiation dose usually to be set being adjusted to an X-ray examination, e.g. based upon a frequency of preceding radiation exposures and/or an age of a patient. The specification of the preliminary target dose may also take place as a function of X-ray parameters of an X-ray examination, e.g. by a radiation dose being determined from a radiation power and an examination duration usually to be set. Preferably, an algorithm is used which specifies a preliminary target dose as a function of X-ray parameters and/or an item of patient information and/or an examination duration. In this context, use can be made of patient information of one or more patients. In the case of a lack of corresponding information, it is likewise conceivable for a physician or a member of medical personnel to enter a preliminary target dose for an X-ray examination at an operating unit of an X-ray device.

By specifying a preliminary target dose, the radiation exposure can be quantified in advance of an X-ray examination. This advantageously makes it possible to compare the radiation dose of an X-ray examination with known limit values.

In one possible embodiment of the method according to the invention, the first dose regulation is configured to reduce stochastic effective doses of a person, at least as a function of an item of patient information. In this context, a person preferably represents a patient which is exposed to an X-ray radiation during an X-ray examination. A reduction of stochastic effective doses can mean that a radiation dose of a patient during the X-ray examination is chosen such that as few radiation energy dispositions occur as possible. Here, the radiation dose is preferably specified based upon an item of patient information, such as an age, a gender or a disease, for example. It is particularly conceivable that a quality of an X-ray image is not optimal when using the first dose regulation, but is sufficient for a loadable representation of physiological and/or pathological structures and medical devices, such as stents and catheters for example.

It is likewise conceivable for a guide value for stochastic effective doses to be smaller than a preliminary target dose of the X-ray examination. In this case, the guide value for stochastic effective doses is preferably not exceeded during the X-ray examination. It is also conceivable, however, for the X-ray parameters to be altered during the X-ray examination for various perspectives, fluoroscopy angles and/or various body regions, and for corresponding adjustments to the radiation power to be made. In addition, one embodiment of the first dose regulation is conceivable, in which the radiation power remains constant over the course of the X-ray examination. Furthermore, when specifying the X-ray parameters of the first dose regulation, it is also possible to take into consideration X-ray parameters of preceding X-ray examinations from a database. In addition to the set parameters, these in particular may also be associated with an assessment of the image quality by the medical personnel. Based upon these assessments, it is possible to automatically adjust the X-ray parameters of the first dose regulation to reduce the radiation exposure of the patient.

By using the first dose regulation, it is advantageously ensured that the radiation dose of the patient is as low as possible. This makes it possible to reduce the risk of long-term damage due to X-ray radiation.

According to a further embodiment, a second dose regulation is configured to avoid deterministic radiation damage to a person, at least as a function of a limit value for deterministic radiation damage. In this context, the person in question preferably represents a patient which is exposed to a direct irradiation as part of the X-ray examination.

Avoiding deterministic radiation damage in particular means that immediate damage as a consequence of an irradiation of the patient is avoided. This can be achieved by observing the limit values for the entrance skin dose specified by law.

Preferably, however, the second dose regulation is configured such that the radiation dose lies below the limit values specified by law. It is also conceivable for the quality of the X-ray image to not be optimal when using the second dose regulation, in favor of a lower radiation exposure of the patient. Furthermore, when specifying the X-ray parameters of the second dose regulation, it is also possible to take into consideration X-ray parameters of preceding X-ray examinations from a database.

In addition to the set parameters, these in particular may also be associated with an assessment of the image quality by the medical personnel. Based upon these assessments, it is possible to automatically adjust the X-ray parameters of the second dose regulation to reduce the radiation exposure of the patient.

By specifying the second dose regulation, it is possible to avoid immediate damage in the irradiated tissue of the person due to an examination with X-ray radiation. In particular, the reduction of the radiation dose compared to the limit values specified by law advantageously makes it possible to reduce the risk of immediate and long-term radiation damage.

In a further embodiment, a guide value for stochastic effective doses of a person can be specified based upon various target groups. In this context, a target group may be represented by a patient and/or a member of medical personnel, for example. Taking into consideration the radiation dose of the patient typically has the highest priority and may represent a standard setting of the medical X-ray device.

In addition to the patient, however, the medical personnel may also be exposed to a radiation exposure, for example if they remain in the treatment room due to a treatment-related or operational measure during the X-ray examination. Particularly in the case of operational measures, an attending physician bears an increased risk of radiation exposure, as he is typically located in the vicinity of the radiation source and can only partially be protected from the radiation by protective clothing.

In X-ray examinations with high radiation power, it may therefore be appropriate to also take into consideration the stochastic effective dose of the attending physician, in addition to the entrance skin dose of the patient. For this purpose, a radiation dose for the physician is estimated based upon the type of the treatment-related or operational measure and/or the radiation dose of the patient, for example. This estimation may for example take place based upon a factor, with which the radiation dose of the patient is converted to that of the attending physician.

It is likewise conceivable, however, for that radiation dose of the physician at a distance from the radiation source to be calculated using the inverse square law. Based upon this estimated radiation dose, the X-ray parameters of the medical X-ray device can be adjusted in order to reduce the radiation dose for the attending physician. In one conceivable operating mode, a second dose regulation is chosen for example such that the entrance skin dose of the patient is not exceeded. At the same time, the parameters of the second dose regulation in the permitted parameter range can be adjusted further, in order to achieve a reduced radiation dose for the attending physician at an estimated distance from the radiation source.

In further conceivable operating modes, the guide value for the stochastic effective dose may also take place solely based upon the radiation exposure of the patient or the attending physician. In this context, both a manual switchover and an automatic switchover between the operating modes mentioned are conceivable. Criteria for an automatic switchover may represent e.g. the type of the X-ray examination, but also effective doses and exposure times of the medical personnel in the treatment room.

By taking into consideration different target groups, it is advantageously possible to achieve a compromise between desired image quality and necessary radiation exposure of the patient and the attending medical personnel.

According to a further embodiment of the method according to the invention, a guide value for stochastic effective doses is specified, at least as a function of a preliminary target dose and/or an item of patient information and/or a frequency of a radiation exposure. The specification of the guide value for stochastic effective doses is preferably performed individually for each patient, as they may have different disease and treatment courses.

Moreover, the frequency of a radiation exposure and the course of the disease may have a significant influence on the cumulative radiation dose of a patient over a treatment period and these are therefore preferably taken into consideration in the dose regulation. For example, the guide value for stochastic effective doses may be set lower for young patients or those with frequent radiation exposure, in order to reduce the risk of subsequent radiation-related diseases.

The patient information required for this purpose is preferably retrieved from a database on an automated basis. It is likewise conceivable, however, for the necessary patient information for specifying the guide value for the stochastic effective dose to be captured based on a questioning of the patient and to be entered by the medical personnel via an interface of the medical X-ray device. The guide value for stochastic effective doses may limit the permissible parameter range of the first dose regulation and thus reduce the radiation dose of the patient.

It is also conceivable for the guide value for stochastic effective doses to have a minimum limit. If the preliminary target dose of the X-ray examination lies below this limit, then an application of the first dose regulation can be disregarded. In this case, the radiation dose of the X-ray examination may be equated with the preliminary target dose. The guide value for stochastic effective doses is typically smaller than the limit value for deterministic radiation damage.

By taking into consideration patient information when specifying the guide value of the stochastic effective dose, it is advantageously possible to adjust the radiation dose for each patient individually.

In a further embodiment of the method according to the invention, a second dose regulation is specified if a preliminary target dose lies above a limit value for deterministic radiation damage. The limit value for deterministic damage, as far as possible, should not be exceeded, in order to avoid immediate skin damage in an irradiated body region of the patient. Therefore, a radiation dose is preferably adjusted by way of the second dose regulation such that an integral of a time-dependent radiation power, in relation to a mass of the body region subjected to fluoroscopy, lies below the limit value for deterministic damage. It is conceivable for the radiation power to vary during the course of an X-ray examination. In addition, it is also conceivable for the radiation power to remain constant over the entire course of the examination.

By restricting the radiation dose by way of the second dose regulation, immediate tissue damage in the irradiated body regions of the patient can be advantageously avoided.

In a further embodiment of the method according to the invention, the first dose regulation is specified if a preliminary target dose lies below a guide value for stochastic effective doses. By applying the first dose regulation, the aim is preferably to reduce a radiation dose of an X-ray examination and therefore a risk of stochastic radiation damage. For this purpose, the radiation dose of the X-ray examination may be specified as deviating from the preliminary target dose, e.g. as a function of an item of patient information and/or a frequency of a radiation exposure.

A reduction of the radiation dose may be applied for example when the patient information gives warning of an upstream treatment history with X-ray radiation or when the patients are minors. Particularly in infants and young persons, it may be appropriate to systematically reduce the radiation dose in order to reduce a risk of later diseases arising from stochastic radiation damage.

Preferably, in this case a parameter range of the first dose regulation is restricted accordingly, in order to reduce the radiation dose compared to the preliminary target dose. In the case of overweight persons or older persons, e.g. patients who are 30 years old, 40 years old and in particular 50 years old or more, the radiation dose to be applied can be reduced in a graduated manner compared to the preliminary target dose, with corresponding indication. In this context, e.g. with advancing age and the same body weight, or with increasing body weight and the same age, the radiation dose may converge with the preliminary target dose in a linear, asymptomatic or exponential manner. By contrast, if there is no indication of an acute risk due to stochastic radiation damage, then the preliminary target dose may also be specified as a setpoint value for the first dose regulation. In these cases, instead of the radiation dose, the image quality of the X-ray images can be used as the preferred regulation variable.

Due to the simplified specification of the first dose regulation based upon the guide value for stochastic effective doses, the robustness of the method is advantageously improved. As a result of adjusting the first dose regulation to individual patient requirements, it is additionally possible to calibrate the radiation dose to the patient and reduce the risk of stochastic radiation damage.

In a further embodiment of the method according to the invention, a dose regulation is switched over automatically as a function of a radiation dose of a person. Here, the radiation dose of a person is preferably monitored. A monitoring of the radiation dose may take place over any given period of time. It is conceivable for the radiation dose to be the result of a number of preceding radiation exposures of a person.

The radiation dose may also, however, be the result of a number of future radiation exposures, which are foreseen e.g. as part of a treatment or of accompanying X-ray examinations. In addition, the radiation dose of a person may also be the result of a combination of preceding and future radiation exposures of a person. It is conceivable in particular for the radiation dose of a person to be monitored continuously during an X-ray examination.

In the event of a deviation of a radiation dose from an anticipated radiation dose, in particular if the limit value for deterministic radiation damage is exceeded, then an adjustment of the dose regulation can thus be made. For example, it is possible to automatically switch over from a second dose regulation to a first dose regulation if the limit value for deterministic radiation damage is exceeded as a consequence of an examination duration which is unexpectedly long.

Due to the automatic switchover of the dose regulation as a function of the radiation dose of a person, it is possible for immediate radiation damage of an X-ray examination to be advantageously avoided.

According to a further embodiment of the method according to the invention, a limit value for deterministic radiation damage and a guide value for stochastic effective doses amount to the same value. In this case, the dose regulation can be specified directly based upon the preliminary target dose and the limit value for deterministic radiation damage. If the preliminary target dose lies above the limit value for deterministic radiation damage, then preferably a second dose regulation is selected, which ensures a radiation dose below the permitted entrance skin dose. If, however, the preliminary target dose lies below the permitted entrance skin dose, then the first dose regulation can be applied, in which the radiation dose is set such that a risk of stochastic radiation damage is reduced.

In this embodiment, the selection of the dose regulation can take place directly based upon the preliminary target dose and the limit value for deterministic radiation damage. The course of the method can be accelerated in an advantageous manner as a result.

In a further embodiment of the method according to the invention, a limit value for deterministic radiation damage and a guide value for stochastic effective doses differ from one another and define a difference range. If the preliminary target dose falls in this difference range, then the dose regulation of the X-ray examination is specified manually. As the difference range lies between the limit value for deterministic radiation damage and the guide value for stochastic effective doses, both the first dose regulation and a second dose regulation can be applied. Due to the necessity of manually specifying the dose regulation, the medical personnel can decide which radiation exposure is applied to the patient on an independent basis, e.g. taking into consideration patient information. This decision can be made anew on each occasion for each patient and each X-ray examination, and can be made independently of other factors.

By manually specifying the dose regulation in the difference range, the complexity of the method and the demands on the processor of the medical X-ray device are advantageously reduced. As a result, the method can also be performed on simple X-ray devices which can be manufactured in a more cost-efficient manner as a result.

In a preferred embodiment of the method according to the invention, the dose regulation is specified by way of a prediction model, which takes into consideration at least a frequency of a radiation exposure and/or a radiation dose of a preceding radiation exposure and/or an item of patient information. In this context, radiation exposures in particular represent medical X-ray examinations or radiotherapies. The frequency of radiation exposure may e.g. relate to events in the future, which can be foreseen as part of a course of treatment.

In addition, the radiation doses already received by the patient can also be taken into consideration. In particular, this may increase the risk of stochastic radiation damage and influence the decision for the radiation doses of subsequent X-ray examinations. It is conceivable for the frequency of such radiation exposures to be extracted directly from a database containing patient information by way of corresponding algorithms, and/or to be entered manually into a digital database of the medical X-ray device by the patient or the medical personnel.

In addition to the factors mentioned, it is also possible for patient information such as an age, a weight, a gender or a course of the disease to be taken into consideration when specifying the radiation dose.

The corresponding information is preferably processed by a prediction model implemented on the controller of the medical X-ray device. Using the prediction model, for example, anticipated radiation exposures of the patient and/or risk factors for stochastic radiation damage can be predicted, based upon which a dose regulation can be specified. Possible methods for estimating the relevant factors are represented by extrapolation methods, regression analyses, exponentially smoothed prediction methods and heuristic and model-based methods, for example. It is conceivable that, for the prediction of the radiation exposure and effective dose of a patient, the patient information of other patients is processed.

By applying prediction models, the medical personnel can advantageously be relieved in relation to specifying individual radiation doses. At the same time, a precise and reproducible specification of the radiation dose can be achieved based upon prediction models.

In a related embodiment, the dose regulation is specified by way of intelligent algorithms, which take into consideration at least a frequency of a radiation exposure and/or a radiation dose of preceding radiation exposures and/or an item of patient information. Intelligent algorithms typically refer to algorithms which emulate human decision-making structures. Examples of such algorithms are represented by expert systems, artificial neural networks and deep learning methods. With the aid of intelligent algorithms, the dose regulation can be determined based upon a large number of directly and indirectly correlated influence factors in comparatively short periods of time.

Possible influence factors are represented by the frequency of a radiation exposure of the patient and the radiation dose of the corresponding radiation exposure, as well as further patient information such as an age, a weight, a gender, a disease or a body region of a patient in question. In addition, it is conceivable to take into consideration further influence factors, such as an assessment of image qualities of various X-ray parameters by the medical personnel or statistical data on the risk of developing tumors or cancer due to radiation exposures, for example.

Moreover, the influence factors mentioned can be combined as desired and/or expanded by further influence factors. In order to train the intelligent algorithms, decisions of the medical personnel are preferably used in the teaching phase. Furthermore, it is conceivable to teach the intelligent algorithms based upon various closed datasets, which comprise radiation doses for various application cases which have been optimized in advance. It is conceivable, instead of or in addition to a strategy for dose regulation, for an entire set of adjusted X-ray parameters to already be output by way of the intelligent algorithms.

By applying intelligent algorithms, a large number of influence factors can be taken into consideration when specifying the radiation dose for a patient. As a result, the method is advantageously able to provide an optimized radiation dose for the patient.

The medical X-ray device according to an embodiment of the invention comprises a controller and in one embodiment, may be embodied to perform a method according to one of the embodiments. The controller of the medical X-ray device may comprise a computing unit (which may be at least one processor, for example), for example, which is preferably embodied to calibrate processes and parameters within the medical X-ray device with one another and to process digital data.

In particular, the medical X-ray device of an embodiment has an interface with which it is possible to access data in a network, on a server or a cloud. In a memory unit of the controller, it is possible to store computer programs and further software, by which a processor of the controller controls and/or carries out a course of a method according to an embodiment of the invention automatically. Moreover, datasets, such as patient information and parameter sets, as well as characteristic curves of the medical X-ray device and its components for example, may also be stored on the memory unit.

A non-transitory computer program product according to at least one embodiment of the invention can be loaded directly into a memory of a programmable computing unit of a medical X-ray device and includes program code segments to carry out a method according to an embodiment of the invention when the computer program product is executed in the computing unit of the medical X-ray device. In this way, the method according to at least one embodiment of the invention can be carried out in a rapid, reproducible and robust manner.

The non-transitory computer program product may be configured to carry out the method steps according to at least one embodiment of the invention via the computing unit. In this context, the computing unit must in each case have the requirements such as, for example, a corresponding RAM, a corresponding graphics card or a corresponding logic unit, in order to be able to carry out the respective method steps efficiently.

The non-transitory computer program product may be, for example, a non-transitory computer-readable medium or may be recorded on a network, a server or a cloud, from where it can be loaded into the processor of a local computing unit which can be directly connected to the medical X-ray device or embodied as part of the medical X-ray device. In addition, control information of the computer program product can be stored on an electronically readable data carrier. The control information of the electronically readable data carrier can be configured such that it carries out a method according to an embodiment of the invention when the data carrier is used in a computing unit of a medical X-ray device. Examples of electronically readable data carriers are a DVD, a magnetic tape or a USB stick, on which electronically readable control information, in particular software (see above) is stored. If this control information (software) is read from the data carrier and stored in a controller and/or computing unit of a medical X-ray device, all the embodiments of the above-described methods according to the invention can be performed.

Figure 1:
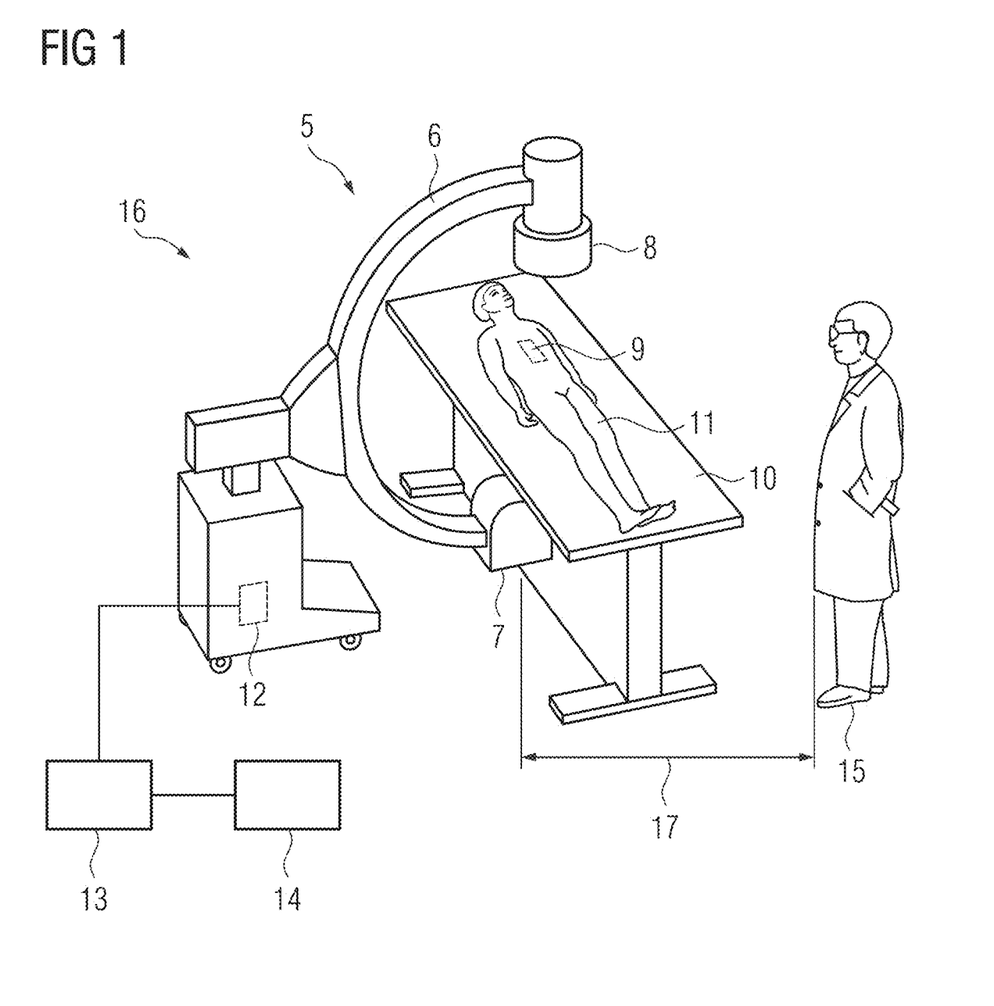
FIG. 1 shows a medical X-ray device according to an embodiment of the invention.

FIG. 1 shows a schematic sketch of an X-ray device 5 according to an embodiment of the invention, which in the present case has a C-arm 6 on which an X-ray emitter 7 and an X-ray detector 8 are arranged opposite one another. The X-ray device is already oriented such that it is possible to record a target area 9 of a patient 11 positioned on a patient couch 10. Via the C-arm 6, the X-ray device formed by the X-ray emitter 7 and the X-ray detector 8 can be moved into various recording positions in relation to a patient 11 positioned on a patient table 10. It is likewise conceivable for a physician or a member of medical personnel (not shown) to be situated adjacent to the patient couch 10, in order to perform treatment-related or operational measures on the patient 11 during the X-ray examination.

The medical X-ray device 5 further has a controller 12, which is embodied for performing the method according to an embodiment of the invention. In this context, the tasks of the controller 12 may e.g. comprise the setting of various X-ray parameters, the selection and implementation of a dose regulation or the calibration of various steps of the image recording and image preprocessing. Furthermore, the medical X-ray device 5 comprises a display unit 13 and an operating unit 14, in order to allow an interaction with a user. In the case of X-ray-supported, operational or treatment-related measures, an attending medical practitioner 15 may also be situated in the treatment room 16, having a distance 17 from the X-ray emitter 7. The distance of the attending medical practitioner from the X-ray emitter 7 may change during the X-ray examination.

A method described herein may also be provided in the form of a computer program which implements the method on the controller 12 when it is executed on the controller 12. An electronically readable data carrier (not shown) with electronically readable control information stored thereon can also be provided, the control information comprising at least one computer program as described and being configured such that, on use of the data carrier in the controller 12 of the X-ray facility 5, it performs a method as described.

Figure 2:
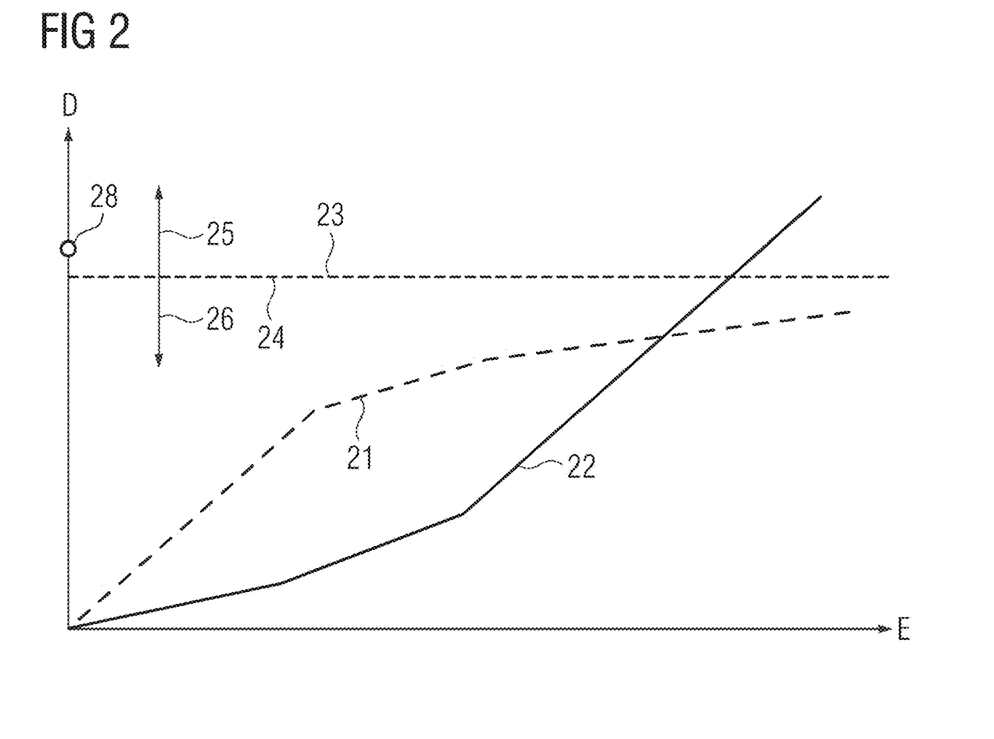
FIG. 2 shows a schematic representation of the selection of a dose regulation.

FIG. 2 shows a schematic dose diagram, which contrasts the radiation effects (E) of deterministic and stochastic radiation events as a function of the radiation dose (D). From the courses of the two curves, it can be gathered that stochastic radiation effects 22 outweigh deterministic radiation effects 21 at a low radiation dose.

In a simple embodiment of the method according to an embodiment of the invention, the limit value for deterministic radiation damage (Dd) 23 and the guide value for stochastic effective doses (Ds) 24 amount to the same value. In this case, the dose regulation of the X-ray examination is solely specified based upon the limit value for deterministic radiation damage 23 as well as the conservatively ascertained preliminary target dose (Dz) 28 of the patient 11. If the preliminary target dose 28, as shown in FIG. 2, lies above the limit value for deterministic radiation damage 23, then the second dose regulation (D2) 25 is specified.

For the second dose regulation 25, the X-ray parameters of the medical X-ray device 5 are set such that the radiation dose of the patient 11 during the X-ray examination remains below the limit value for deterministic radiation damage 23. If the preliminary target dose lies below the limit value for deterministic radiation damage 23, however, then the first dose regulation (D1) 26 is specified as part of the method according to an embodiment of the invention.

For the first dose regulation 26, inter alia patient information such as the patient age, the patient weight and the treatment history of the patient for example are used as decision factors in order to reduce the radiation dose of the X-ray examination compared to the preliminary target dose 28. For example, the controller 12 may be connected to a network or a cloud via an interface (not shown), in order to store the necessary patient information as datasets on a local memory unit and process this accordingly for the determination of the X-ray parameters. It is likewise conceivable for the necessary patient information to be stored directly on the memory unit of the medical X-ray device 5 according to an embodiment of the invention.

Figure 3:
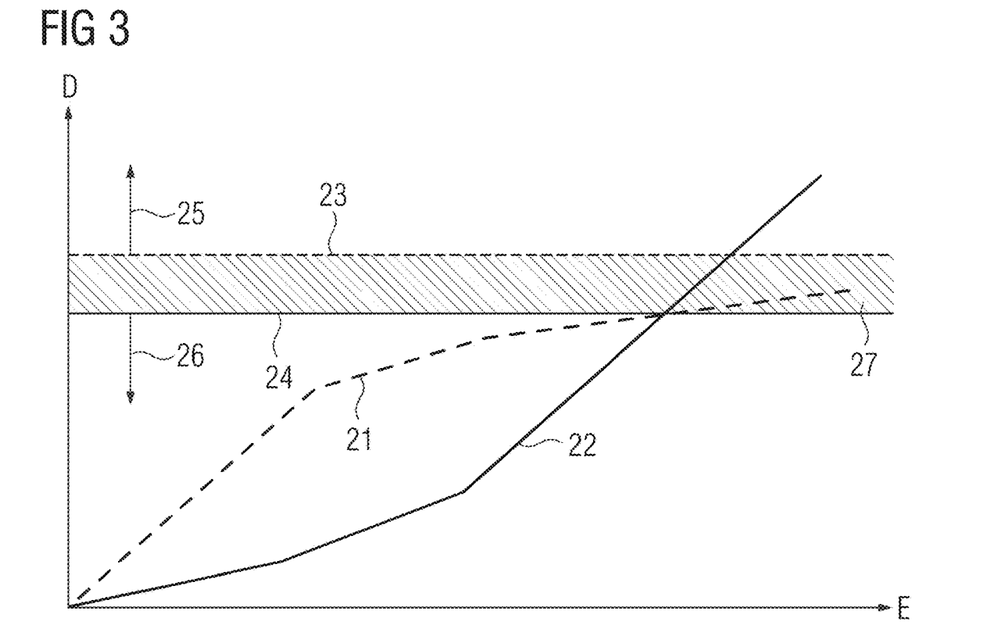
FIG. 3 shows a schematic representation of the selection of a dose regulation.

FIG. 3 illustrates an embodiment of the method according to an embodiment of the invention, in which the guide value for stochastic effective doses 24 and the limit value for deterministic radiation damage 23 differ from one another. In the case of a preliminary target dose 28 above the limit value for deterministic radiation damage 23, the second dose regulation 25 is specified, while the below the guide value for stochastic effective doses 24 the first dose regulation 26 is specified. The difference range 27 between the limit value for deterministic radiation damage 23 and the guide value for stochastic effective doses 24 is not initially assigned to any dose regulation. If the preliminary target dose 28 lies in this difference region 27, then different methods for specifying the dose regulation can be applied. In addition to a manual specification of the dose regulation by the medical personnel, it is e.g. also possible for prediction models or intelligent algorithms for supporting the medical personnel or for automatically specifying the dose regulation to be used by the medical X-ray device 5.

Figure 4:
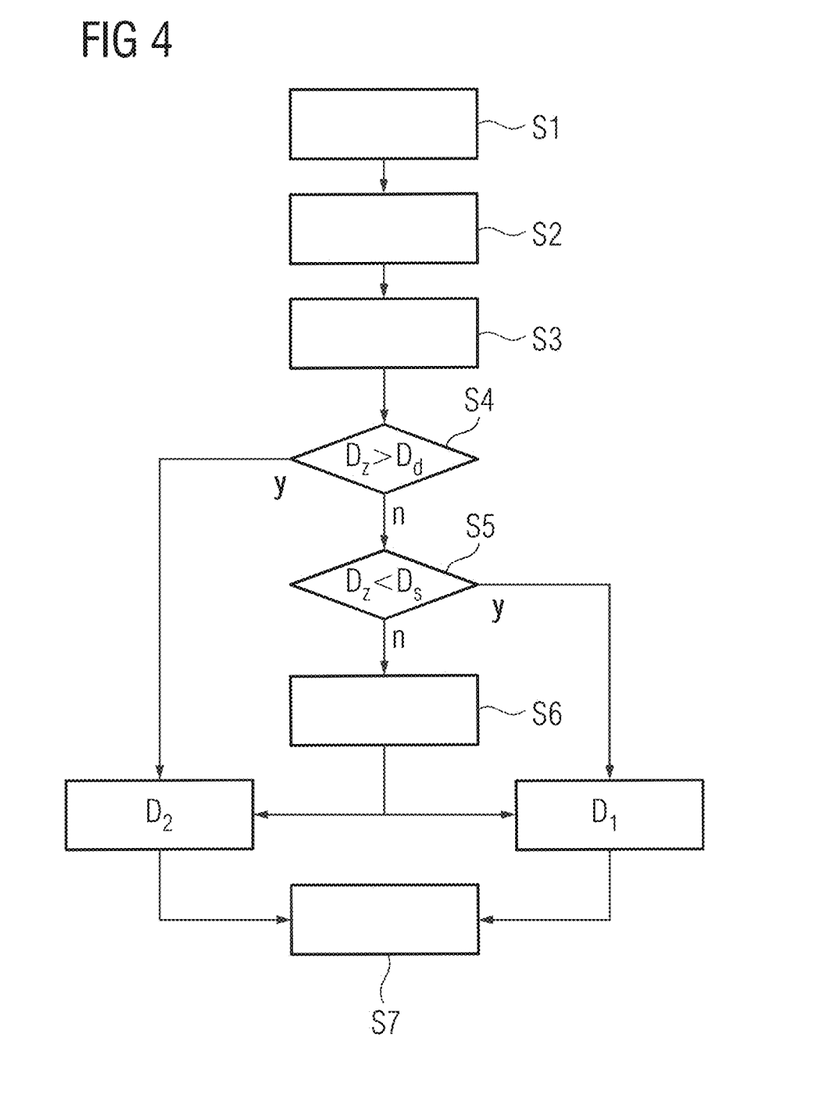
FIG. 4 shows a possible flow chart of a method according to an embodiment of the invention.

FIG. 4 shows a schematic flow diagram of a preferred embodiment of the method according to the invention. In advance of the X-ray examination, patient information of a patient 11 to be examined is called up at the medical X-ray device 5. This may be stored permanently on a memory unit of the controller 12 of the medical X-ray device 5, for example, or may be called up via a network or a cloud. In a first method step S1, an analysis of patient information is performed, in order to obtain relevant data for the determination of the preliminary target dose 28 and of the dose regulation to be specified. The analysis of the patient information may take place by way of an algorithm, for example, which is executed on a computing unit of the controller 12 and searches for corresponding entries in a digital file of the patient in question and/or another patient and/or further patients.

In a further step S2, the preliminary target dose 28 in the simplest case is determined based upon the treatment method and/or the target region of the X-ray examination. Optionally, it is also possible for the medical personnel to enter a value for the preliminary target dose directly by way of an operating unit 14 of the medical X-ray device 5. In a third step S3, an individual guide value for the stochastic effective dose of the patient 11 is specified while taking into consideration the patient information analyzed in step S1. In this context, for example, use can be made of information regarding the age, the weight and radiation exposures of the patient 11 from the past and/or planned for the future, in order to make an adjustment of the radiation dose which is as suitable as possible.

In a subsequent step S4, the value of the preliminary target dose (Dz) 28 is first compared with the limit value for deterministic radiation damage (Dd) 23. If the value of the preliminary target dose 28 lies above the limit value for deterministic radiation damage 23 (Dz>Dd), then the second dose regulation (D2) 25 is specified for the regulation of the radiation dose of the patient 11 during the X-ray examination. If the value of the preliminary target dose 28 lies below the limit value for deterministic radiation damage 23 ($Dz<Dd$), then a further method step S5 is initiated with a query of whether the value of the preliminary target dose 28 lies below the guide value for stochastic effective doses (Ds) 24 ($Dz<Ds$). If this is the case, then the first dose regulation (D1) 26 is specified for the setting of the X-ray parameters of the X-ray examination.

If the value of the preliminary target dose 28 in method step S5, however, lies above the guide value for stochastic effective doses 24, then the preliminary target dose 28 lies in the difference range 27 ($Dd>Dz>Ds$). In this case, the specification of the dose regulation may take place manually by way of the medical personnel in method step S6. Preferably, however, in method step S6, prediction models or intelligent algorithms are used in order to specify the dose regulation of the X-ray examination automatically or to provide information regarding individual radiation risks, which can be used by the medical personnel as the basis for deciding the specification of the dose regulation.

After specifying a dose regulation, the X-ray method is performed with the corresponding dose regulation, in order to generate image data of the patient 11. The performance of the X-ray examination with the specified dose regulation represents the method step S7 of the method according to an embodiment of the invention. In this context, the X-ray parameters of the medical X-ray device may be altered during the X-ray examination in the permitted parameter range of the respective dose regulation. The radiation dose of the patient 11, however, should not exceed the guide value for stochastic effective doses 24.

In a variant form of the flow chart shown in FIG. 4, method step S5 may also be performed before method step S4. The order of these two method steps is irrelevant for the ability to perform the method according to an embodiment of the invention. In an alternative embodiment, method step S3 may also take place before method step S2, provided that the preliminary target dose is not required for a specification of the guide value for stochastic effective doses. This may take place if the guide value for stochastic effective doses is solely determined based upon an item of patient information.

In a further embodiment of the method according to the invention, as described in the embodiment in FIG. 3, it is possible to dispense with a determination of the guide value for the stochastic effective dose 24 in its entirety. In this case, the adjustment of the radiation dose to the individual patient requirements takes place e.g. via the first dose regulation 26. It is likewise conceivable for the guide value for stochastic effective doses 24 to be created solely as a function of limited patient information, which may be requested from the patient as part of the examination preparation. For example, this may be information regarding the patient age and the type of X-ray-based examination method.

For the performance of the method according to an embodiment of the invention, it is in particular not necessary for the guide value for stochastic effective doses 24 to limit the parameter range of the first dose regulation 26. It is likewise conceivable for this to solely be used to specify a dose regulation. In this case, the radiation dose of the patient 11 is adjusted by the specified dose regulation while taking into consideration the individual patient requirements.

Although the invention has been illustrated and described in greater detail with the preferred example embodiment, the invention is not restricted by the examples disclosed and other variations can be derived therefrom by the person skilled in the art without departing from the protective scope of the invention.

Although example embodiments have been described in detail, the example embodiments are not restricted by the examples given and other variations can be derived therefrom by a person skilled in the art without departing from the protective scope of example embodiments.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for specifying radiation dose regulation of a person for an examination with a medical X-ray device including one or more controllers, the method comprising:
   specifying, by the one or more controllers, X-ray parameters of an X-ray examination based upon patient information stored in a memory; and
   specifying, by the one or more controllers, a recommended dose regulation of the X-ray examination as a function of the X-ray parameters specified and at least one of a limit value for deterministic radiation damage or a guide value for stochastic effective doses, the recommended dose regulation including at least a first dose regulation configured to avoid deterministic radiation damage to a person, at least as a function of a limit value for deterministic radiation damage,
   wherein the recommended dose regulation is for adjusting an X-ray dose of the medical X-ray device.

2. The method of claim 1, wherein the specifying the recommended dose regulation includes
   specifying a preliminary target dose based upon at least one of patient information, X-ray parameters or an examination duration of an X-ray examination, and
   specifying the recommended dose regulation as a function of a comparison of the preliminary target dose with at least one of a limit value for deterministic radiation damage or a guide value for stochastic effective doses.

3. The method of claim 1, wherein the specifying the recommended dose regulation comprises:
   configuring a second dose regulation to reduce stochastic effective doses of a person, at least as a function of an item of patient information.

4. The method of claim 1, further comprising:
   specifying a guide value for stochastic effective doses of a person based upon target groups.

5. The method of claim 1, further comprising:
   specifying a guide value for stochastic effective doses as a function of at least one of a preliminary target dose, an item of patient information, or a frequency of a radiation exposure.

6. The method of claim 1, further comprising:
   specifying the recommended dose regulation as the first dose regulation in response to a value of a preliminary target dose being above a limit value for deterministic radiation damage.

7. The method of claim 1, wherein the recommended dose regulation includes at least the first dose regulation and a second dose regulation, the method further comprising:
specifying the recommended dose regulation as the second dose regulation in response to a value of a preliminary target dose being below a guide value for stochastic effective doses.

8. The method of claim 1, wherein the recommended dose regulation includes at least the first dose regulation and a second dose regulation, the method further comprising:
switching the recommended dose regulation between the first dose regulation and the second dose regulation as a function of a radiation dose of a person.

9. The method of claim 1, wherein a limit value for deterministic radiation damage and a guide value for stochastic effective doses are a same value.

10. The method of claim 1, wherein a limit value for deterministic radiation damage and a guide value for stochastic effective doses differ from one another and define a difference range, the method further comprising:
specifying the recommended dose regulation manually in response to a preliminary target dose being in the difference range.

11. A non-transitory computer program product, directly loadable into a memory of a programmable computing unit of a medical X-ray device, storing program code segments to carry out the method of claim 1 when the program code segments are executed in the computing unit of the medical X-ray device.

12. The method of claim 2, wherein the specifying the recommended dose regulation comprises:
configuring a second dose regulation to reduce stochastic effective doses of a person, at least as a function of an item of patient information.

13. The method of claim 10, further comprising:
specifying the recommended dose regulation manually by way of a prediction model, the prediction model considering at least one of a frequency of a radiation exposure, a radiation dose of preceding radiation exposures or an item of patient information.

14. The method of claim 10, further comprising:
specifying the recommended dose regulation manually by way of intelligent algorithms, taking into consideration at least one of a frequency of a radiation exposure, a radiation dose of preceding radiation exposures, or an item of patient information.

15. A medical X-ray device, comprising:
processing circuitry configured to cause the medical X-ray device to
specify X-ray parameters of an X-ray examination based upon patient information stored in a memory, and
specify a recommended dose regulation of the X-ray examination as a function of the X-ray parameters and at least one of a limit value for deterministic radiation damage or a guide value for stochastic effective doses, the recommended dose regulation including at least a first dose regulation configured to avoid deterministic radiation damage to a person, at least as a function of a limit value for deterministic radiation damage,
wherein the recommended dose regulation is for adjusting an X-ray dose of the medical X-ray device.

16. The method of claim 2, further comprising:
specifying a guide value for stochastic effective doses of a person based upon target groups.

17. The medical X-ray device of claim 15, wherein the processing circuitry is further configured to cause the medical X-ray device to:
calibrate processes and parameters within the medical X-ray device with one another; and
process digital data.

18. The medical X-ray device of claim 15, further comprising:
an interface configured to access data from at least one of a network, a server or a cloud.

19. A method for specifying radiation dose regulation of a person for an examination with a medical X-ray device including one or more controllers, the method comprising:
specifying, by the one or more controllers, X-ray parameters of an X-ray examination based upon patient information stored in a memory;
specifying, by the one or more controllers, a recommended dose regulation of the X-ray examination as a function of the X-ray parameters specified and at least one of a limit value for deterministic radiation damage or a guide value for stochastic effective doses, the recommended dose regulation including at least one of a first dose regulation or a second dose regulation; and
specifying the recommended dose regulation as the first dose regulation in response to a value of a preliminary target dose being below a guide value for stochastic effective doses,
wherein the recommended dose regulation is for adjusting an X-ray dose of the medical X-ray device.

20. A method for specifying radiation dose regulation of a person for an examination with a medical X-ray device including one or more controllers, the method comprising:
specifying, by the one or more controllers, X-ray parameters of an X-ray examination based upon patient information stored in a memory;
specifying, by the one or more controllers, a recommended dose regulation of the X-ray examination manually in response to a preliminary target dose being in a difference range, the specifying being performed as a function of the X-ray parameters specified and at least one of a limit value for deterministic radiation damage or a guide value for stochastic effective doses, wherein the limit value for deterministic radiation damage and the guide value for stochastic effective doses differ from one another and define the difference range; and
specifying the recommended dose regulation manually in response to a preliminary target dose being in the difference range,
wherein the recommended dose regulation is for adjusting an X-ray dose of the medical X-ray device.

21. A method for specifying radiation dose regulation of a person for an examination with a medical X-ray device including one or more controllers, the method comprising:
specifying, by the one or more controllers, X-ray parameters of an X-ray examination based upon patient information stored in a memory; and
specifying, by the one or more controllers, a recommended dose regulation of the X-ray examination manually by way of a prediction model, the prediction model considering at least one of a frequency of a radiation exposure, a radiation dose of preceding radiation exposures, or an item of patient information, the specifying being performed as a function of the X-ray parameters specified and at least one of a limit value for deterministic radiation damage or a guide value for stochastic effective doses, wherein the recommended dose regulation is for adjusting an X-ray dose of the medical X-ray device.

22. A method for specifying radiation dose regulation of a person for an examination with a medical X-ray device including one or more controllers, the method comprising:
   specifying, by the one or more controllers, X-ray parameters of an X-ray examination based upon patient information stored in a memory; and
   specifying, by the one or more controllers, a recommended dose regulation of the X-ray examination manually by way of intelligent algorithms, taking into consideration at least one of a frequency of a radiation exposure, a radiation dose of preceding radiation exposures, or an item of patient information, the specifying being performed as a function of the X-ray parameters specified and at least one of a limit value for deterministic radiation damage or a guide value for stochastic effective doses,
   wherein the recommended dose regulation is for adjusting an X-ray dose of the medical X-ray device.

23. A medical X-ray device, comprising:
   processing circuitry configured to cause the medical X-ray device to
      specify X-ray parameters of an X-ray examination based upon patient information stored in a memory,
      specify a recommended dose regulation of the X-ray examination as a function of the X-ray parameters and at least one of a limit value for deterministic radiation damage or a guide value for stochastic effective doses, the recommended dose regulation including at least one of a first dose regulation or a second dose regulation, and
      specify the recommended dose regulation as the first dose regulation in response to a value of a preliminary target dose being below a guide value for stochastic effective doses,
   wherein the recommended dose regulation is for adjusting an X-ray dose of the medical X-ray device.

* * * * *